United States Patent [19]

Lerailler et al.

[11] Patent Number: 4,883,478

[45] Date of Patent: Nov. 28, 1989

[54] PROCESS FOR PREPARING A LIQUID-ABSORBING COMPOSITION

[75] Inventors: Eric Lerailler, Lognes; Michel Pierre, Mulhouse; Bernard Thiriet, Juvisy s/Orge; Jean Wacquez, Courbevoie, all of France

[73] Assignee: Beghin-Say, S.A., Thumeries, France

[21] Appl. No.: 88,110

[22] PCT Filed: Nov. 21, 1986

[86] PCT No.: PCT/FR86/00398

§ 371 Date: Sep. 21, 1987

§ 102(e) Date: Sep. 21, 1987

[87] PCT Pub. No.: WO87/03208

PCT Pub. Date: Jun. 4, 1987

[30] Foreign Application Priority Data

Nov. 22, 1985 [FR] France ................. 85 17351

[51] Int. Cl.⁴ ............... A61F 13/16; A61F 13/18; A61F 13/20
[52] U.S. Cl. ................. 604/360; 604/336; 604/364; 604/904; 424/445; 428/317.7
[58] Field of Search ............ 128/156; 424/DIG. 13, 424/445, 447; 514/778, 779, 781, 774; 428/317.7, 316.6; 604/304, 336, 360, 364, 367, 897, 904

[56] References Cited

U.S. PATENT DOCUMENTS

| | | | |
|---|---|---|---|
| 3,767,784 | 10/1973 | Gluck | 514/774 |
| 4,253,460 | 3/1981 | Chen et al. | 128/156 |
| 4,307,717 | 12/1981 | Hynes et al. | 128/156 |
| 4,394,930 | 7/1983 | Korpman | 428/316.6 |
| 4,415,388 | 11/1983 | Korpman | 604/336 |
| 4,486,488 | 12/1984 | Pietsch et al. | 514/781 |
| 4,538,603 | 9/1985 | Pawelchak et al. | 128/156 |

OTHER PUBLICATIONS

Hawley's Condensed Chemical Dictionary, 11th Ed., Sax et al. (editors), (1987, 1981, 1971 ...), pp. 34, 227, 580–581.

Takahashi et al, Japanese Patent Abstract, Appl. No. 58-62959, Oct. 26, 1984.

*Primary Examiner*—Richard J. Apley
*Assistant Examiner*—Paul Prebilic
*Attorney, Agent, or Firm*—A. W. Breiner

[57] ABSTRACT

Method for the preparation of an absorbent composition intended particularly to the absorption of physiological liquids such as urine, secretions from wounds, blood, etc. The method comprises the preparation of a concentrated solution of mono- and/or disaccharide in water, particularly saccharose. To said solution there is admixed a predetermined amount of superabsorbent up to obtaining a homogenous paste which is dried to an extent such that the water content is brought down to a value comprised between 2 and 15%. It is possible to introduce with the superabsorbent a portion of the oligosaccharide in the form of powder. The resultant mixture comprises less than 50% of superabsorbent and preferably between 1 and 30% in the case of a dressing.

11 Claims, No Drawings

PROCESS FOR PREPARING A LIQUID-ABSORBING COMPOSITION

The invention relates to a process for preparing an absorbing composition with particular application in the absorption of physiological fluids: urine, wound secretions, blood, etc. This composition can be used as a dressing in the treatment of wounds or as an additive in disposable articles of hygiene, notably for female hygiene.

The absorbing compounds referred to below are polymers, hydrophilic macromolecules which are virtually insoluble in water and swell in the presence of water until they acquire the consistency of a gel. These superabsorbents, also called hydrogels, water-retaining agents or improved retention additives, abbreviated IRA, are solids able to gel liquid 10 to 1000 times their own weight. The gels obtained have the property of not desorbing liquid easily when subjected to pressure which deforms the mass. For this reason, superabsorbents have numerous applications in agriculture for water retention, and in hygiene for the absorption of physiological fluids such as urine and blood where they are used as additives to improve absorption capacity of the absorbing mass, fibrous material, generally cellulose foam, comprising diapers, baby slips, sanitary towels and tampons. They are also used in medicine for the treatment of wounds. The most common compounds are alginates, cross-linked carboxymethylcellulose, branched starches and in synthetic derivatives of the acrylamide or acrylate type.

These compounds each have their own physicochemical characteristics, such as the speed of gelling and absorption capacity. Nonetheless, even for a given compound these characteristics vary considerably depending on the type of fluid absorbed: pure water, urine, serum, blood.

Hence, the absorption capacity can be divided by 10 when water is replaced by salt water, and the gelling speed is considerably reduced. This is a drawback in the case, for example, of diapers for infants. Indeed, if the child urinates and the urine is not absorbed rapidly enough, when the diaper is changed there may be a loss of liquid.

These compounds are, moreover, costly. For disposable articles of hygiene manufactured on a large scale, where costs must be finely judged, there is a continuous need for studies of more economical products.

In order to improve the absorption speed of the superabsorbent, attempts have already been made to introduce them dry or disperse them in mineral or organic powders, such as cellulose (U.S. Pat. No. 4055184), inert materials, such as cellulose, clays (patents DE No. 2264027, JP No. 13543575), silica or aluminum (U.S. Pat. No. 3932322), carboxymethylcellulose (U.S. Pat. No. 4043921, FR No. 2388901), and in water-soluble powders (EP No. 71063), which may be mono- and/or disaccharides (patent JP No. 59 89169).

The aim of the invention is to prepare an absorbing composition from any superabsorbent, with improved qualities by comparison with the corresponding superabsorbent, or with at least comparable qualities but of reduced cost, hence improving value for money.

The absorbent composition is usable in particular for absorption of physiological fluids, as an addition in disposable articles of hygiene, notably for female hygiene, or as a dressing in the treatment of wounds. It is prepared from a superabsorbent and at least one oligosaccharide chosen from among disaccharides such as sucrose, lactose, maltose, cellobiose, monosaccharides such as glucose or fructose, higher sugars and glucose syrups.

The invention applies to all known superabsorbents, but significant results were obtained in particular with superabsorbents of the acrylate type.

The superabsorbent can be chosen from among a large class of compounds, such as inorganic (silicates, etc.) or organic compounds capable of absorbing and retaining liquid even when subject to moderate pressure. The organic compounds include, alginates, guar gum, agar, carrageen and other compounds extracted from natural products; cellulose derivatives including cross-linked carboxymethylcellulose (example: Akucell from Enka, Akzo/Holland), hydroxyethycelluloses, non-ionic compounds unaffected by saline solutions; starch derivatives such as polyacrylate starches (example: SANWET from Sanyo Chemical/Japan), synthetic polyacrylates (examples: AQUAKEEP from Seitetsu/Japan or LUQUASORB from Stockhausen/Germany, prepared by an inverted suspension process, AQUALIC from Nippon Shokobai/Japan and FAVOR from Stockhausen/Germany, prepared by a process in aqueous solution), polyacrylamide-polyacrylate copolymers, or polyethylenoxides, polyvinylalcohols, polyvinylethers, copolymers of ethylenemaleic acid anhydrides, polyvinylpyridines, polyvinylmorpholenones, derivatives of vinylsulfonic, acrylic, metacrylic acids, etc.

In general these molecules exhibit a modest degree of cross-linking so that they swell but do not dissolve in aqueous solutions. They are cross-linked by the action of heat (spontaneous cross-linking), or by covalent, ionic (di- or trivalent salts) or hydrogen bonding, or by Van der Waals forces.

Sucrose is the preferred sugar since it is simple to use and is more stable bacteriologically than a simple sugar, but other surgars are equally convenient.

In accordance with the invention, the composition is prepared by wet mixing, a surprising result of sugar syrup-superabsorbent synergy. Indeed, bearing in mind the evident interactions between water and superabsorbent, the methods for use of the latter avoid liquid, and more specifically, aqueous phases. We have found that the composition could be prepared easily by incorporation of the superabsorbent in a concentrated solution of sugar, notably sucrose. Such 60 to 80 Brix syrups, or even pastry fondants, represent liquid solvent media, in which the thermodynamic activity of water tightly bound to sugar molecules decreases. Under these conditions, the water-superabsorbent interactions are completely modified and it is possible to prepare homogeneous pseudo-solutions of superabsorbent and sugar which only gel after a certain period of contact.

The invention is characterized in that the process comprises the following steps:

preparation of a concentrated solution of mono- and/or disaccharide in water, incorporation of a determined quantity of superabsorbent corresponding to the proportion of superabsorbent desired in the final composition, kneading of the mixture until a homogeneous paste is obtained, if necessary, drying of the paste to a determined dryness.

Not all the mono- and/or disaccharide can be provided by the concentrated solution. According to a preferred embodiment of the invention, part is provided in the form of powder and is incorporated into the mixture either at the same time as the superabsorbent, or during kneading. This variant allows better control of the viscosity.

According to the preferred embodiments, additives can be admixed before or during the kneading step in order to confer upon the mixture specific activities; zinc oxides, enzymes, amino acids, mineral or organic salts or acids, vitamins, antibiotics, antimicrobials, surfactants. It is also possible to add natural or synthetic textile fibers which will increase the speed of absorption of liquid in the mixture, by capillarity.

The mixture obtained after drying, without addition of plastifier, is very hard and abrasive. It can be broken up, ground and screened to granules of the required size.

The addition of controled concentrations of plastifiers or solvents to facilitate the technological embodiment or use, such as polyols exemplified by glycerine, polyethylene glycol, polyvinyl alcohol, polyvinyl pyrrolidone or isopropyl alcohol, for example, provide plastic masses which at 40° or 50° C. can be laminated, extruded, stuck onto a film or textile or plastic fabric, cold ground, etc. Depending on the plastifier content, products are obtained which in the cold are characterized by persistent plasticity, particularly suitable for the treatment of wounds.

The absorbent composition has an application as an additive in disposable articles of hygiene where it is incorporated in absorbing masses generally comprising fibers, notably cellulose foam, so as to improve their absorption capacity. In this case a preferred embodiment of the composition comprises at least 15% of superabsorbent.

The composition has a special application in the treatment of wounds since it contains sugar. It has long been known that sugar promotes cicatrization, whether in the form of simple powdered kitchen sugar or honey. Its beneficial effects are essentially due to its bactericidal and/or bacteriostatic activity, since when it absorbs secretions from the wound, the water activity Aw imposed by the sugar is too low to allow growth of microorganisms in the wound. The water activity is defined as the ratio of the pressure of the saturating vapor of a solution to that of pure water. For a saturated sucrose solution, for example, the value of Aw at room temperature is 0.86. This value is lower than the water activity at which development is inhibited for pathogens living in wounds. Hence, the microorganisms causing infection are unable to develop and tissular cicatrization is faster. The known method of applying sugar is very simple; after cleansing and drying of the wound with a compress, sugar is evenly poured into the opened wound. A dry adhesive dressing is then placed over the wound to keep the syrup that forms in place.

The absorbing composition simplifies treatment by the action of the superabsorbent which gels and binds exudate with improved efficacy. The composition forms a compact mass. This mass, which is easy to remove, facilitates debridement of wounds and the changing of dressings, and hence improves patient comfort and the rapidity of treatment. For an application of this type, a preferred mixture comprises between 1% and 30% of superabsorbent to give maximum therapeutic efficacy.

Further details of the method of preparation and comparative tests are given below:

This method of preparation can be illustrated by the following example. A sample of sucrose syrup at 80 Brix is used hot so as to avoid recrystallization, i.e. 500 g of syrup, 400 g of sugar and 100 g of water. The hot syrup is poured into a double-jacketed heated mixer (of the Guedu type, for example), which comprises a Z-shaped stirring rod. A plastifier may be added (in our case 37.5 g of glycerol), which helps decrease viscosity and water activity. While mixing, superabsorbent is admixed in a single addition, which in our case was 50 g of product available from Sanyo Chemical/Japan under the brand-name SANWET, reference IM1000. In a few seconds a thick, translucent slightly sticky mass is obtained. To complete the preparation of the compound, and obtain the desired sugar-superabsorbent proportions, bearing in mind the conditions imposed by the type of drying, it may be necessary to add sugar, in our case 100 g of non-amylaceous powdered sugar. The stirring rod of the mixer is allowed to rotate for a few more seconds until a plastic and non-sticky homogeneous block is formed. The block can be extruded through a draw plate or laminated in the form of a plate on a marble, or pressed between two jaws of a hydraulic press. The product is then oven-dried, for example, to give a dry matter content ranging between 85% and 98%, preferably from 92% to 96%.

In the case where an adequate quantity of plastifier is used, after moderate drying a mass is obtained which is sufficiently plastic to be worked or granulated for example in a granulator of the Frewitt type.

A preferred embodiment of the invention consists in preparing a mixture of sugar and superabsorbent and spreading it on a textile support. After oven-drying, a supple composite is obtained which can be mechanically cut and used as a dressing for wounds.

For this application, the method allows homogeneous incorporation of chemical compounds or pharmaceuticals useful for the treatment of wounds:
zinc oxide, up to approximately 10% of the total mass,
zinc dioxide, up to approximately 10% of the total mass,
surfactants, up to approximately 0.2% of the total mass,
enzymes, particularly proteases, amino acids, organic or
   mineral acids or salts, vitamins, antibiotics, antimicrobials, bacteriostatics, colorants, perfumes, etc.

During the preparation, it is also possible to add a volatile diluent, isopropanol for example, which lowers the viscosity and facilitates dispersion and the preparation of a plastic mass. The diluent will be largely eliminated during drying.

The preferred sugar is sucrose, but it may comprise other types of sugar, for example 0 to 15% glucose syrup, 0 to 10% sorbitol, lactose, etc.

The process for the preparation according to the invention can also be used so as to allow continuous production of the absorbing composition. An extruder, which may be of two-screw type, is used to this effect. The saturated sugar syrup at 60–80 Brix, with added plastifier, glycerol for example, is introduced at constant flow between the screws of the extruder. The powdered superabsorbent dry-mixed with powdered sugar is simultaneously introduced into the feed hopper.

Because of these very flexible operating conditions, the extruder only subjects the moving matter to weak shearing stress thus avoiding impairment of the qualities of the superabsorbent. The mixture remains inside the extruder for 15 to 60 seconds. Heating elements may be used to facilitate plastification and control viscosity, although the latter should not be reduced to the point where the product becomes too liquid.

After extrusion, a homogeneous mixture is obtained which can be laminated between two cylinders, and then placed on any support. A one- or multi-hole draw plate may be fitted at the extruder outlet to give a filamentous product. Before shaping of the mixture, it is possible to fit an appropriate heating device (infrared, microwaves) to dry the mixture to the desired extent.

We prepared a homogeneous mixture of this kind from 20 kg of starting products, mixed in the following proportions:

| dry mix: | powdered sugar | 9.3 kg |
|---|---|---|
| | superabsorbent | 1.11 kg |
| syrup: | sucrose | 5.5 kg |
| | water | 2.87 kg |
| | glycerol | 1.11 kg |

In order to specify and quantify the properties of the products prepared according to the process of the invention, comparative tests were carried out to evaluate absorption of salt water (NaCl 10 g/l + 150 ppm surfactant), a fluid comparable to serum and lymph (for example, an injectable solution for perfusion available from Laboratoire R. Bellon under the brand name Plasmion) and a blood formula (of composition: bovine blood 85%, 15% salt water-9 g/l NaCl, with the addition of an anticoagulant, sodium heparinate 0.025 g/l). Depending on the origin of the bovine blood, the physiological composition varies, as shown by the test results in comparative series, which are designated Formula A, Formula B and Formula C. The absorption evaluation tests are given below:

(I) Retention R30

This method allows evaluation of the capacity for retention of a liquid by a superabsorbent. A sanitary towel containing 0.5 g of pure superabsorbent dispersed in variable quantities of sugar and possibly additives was immersed for 30 minutes in liquid. After centrifugation at 1100 g for 60 seconds, the quantity of liquid absorbed by the sample was calculated using the difference between the absorption of a control towel without sample and that of the towel containing sample. The retention R 30 was expressed in grams of liquid absorbed per gram of superabsorbent.

For all calculations, it was assumed that the sugar did not dissolve in the liquid phase (saline or blood). The R30 values obtained were the minimum theoretical values.

(II) Gelling test (vortex test)

The gelling test measures the speed and maximum absorption capacity of a superabsorbent gel. A determined mass of sample was poured directly into a 150 ml beaker (diameter 55 mm) containing 100 ml of test liquid at a given temperature stirred at 600 rpm by a magnetic stirring bar (length 45 mm, diameter 8 mm), and the time required for the vortex to disappear was determined. A series of tests were carried out using samples of varying mass. The absorption by gelling as a function of time is given by an experimental law of the following type:

$$\frac{1}{a} = \frac{1}{G} + \frac{1}{V_0(t - T_0)}$$

Where
a = absorption in g/g
G = maximum absorption capacity in g/g
Vo = initial gelling speed in g/g/s
To = gelling delay time or wetting time in seconds All values are expressed for 1 g of superabsorbent in the samples.

A regression analysis was used to select the best correlation element as a function of the assumption concerning the value of G. This analysis allows selection of optimal values for the coefficients G, Vo and To, which characterize gelling.

To illustrate the present invention, the following products were prepared and their properties tested by the absorption evaluation methods described above.

EXAMPLE 1

Mixtures of sucrose and AQUAKEEP superabsorbent were prepared. The mixtures were vacuum oven-dried, ground and screened. The 100–500 micron fraction was tested.

TABLE 1a

| | | Retention test R30 | | |
|---|---|---|---|---|
| | | Salt water | Blood formulae 35° C. | |
| Sucrose % | AQUAKEEP % | 35° C. g/g | A g/g | B g/g |
| 100 | 0 | 0 | 0 | 0 |
| 93,5 | 6,5 | — | 18 | 13,5 |
| 90,9 | 9,1 | 47 | 16,5 | 11 |
| 85 | 15 | — | — | 12 |
| 80 | 20 | 47 | — | 11 |
| 70 | 30 | 41 | — | 42 |
| 0 | 100 | 49 | 12 | 7 |

Synergy of more than 50% was noted in wet mixing for the absorption of blood.

For the absorption of salt water, the qualities of the superabsorbent were maintained. The absence of synergy with salt water shows that synergy with blood is not associated with the physical accessibility of the sample to the liquid. In addition, values for retention R30 in salt water were characteristic of its content in the sample.

TABLE 1b

| | | Vortex test | | | | | | | | | |
|---|---|---|---|---|---|---|---|---|---|---|---|
| | | Salt water Plasmion | | | | | | Blood formulae 35° C. | | | |
| | | 35° C. | | | 35° C. | | | B | | | C |
| Sucrose % | AQUAKEEP % | G | Vo | To | G | Vo | To | G Vo To | | | G Vo To |
| 93,5 | 6,5 | 300 | 5,8 | 8 | 145 | 3,7 | 6 | 183 2,9 0 | | | 243 4,2 0 |
| 90,9 | 9,1 | 220 | 5,9 | 0 | 115 | 6,6 | 7 | 354 4 0 | | | 323 4,3 0 |
| 85 | 15 | 192 | 14 | 12 | 130 | 8,1 | 9,5 | 138 6 13 | | | 254 2,5 0 |
| 80 | 20 | — | — | — | — | — | — | 149 2,9 0 | | | 315 2,7 0 |
| 70 | 30 | 164 | 24 | 4 | 148 | 7,5 | 3 | — — — | | | — — — |

TABLE 1b-continued

| | | Vortex test | | | | Blood formulae 35° C. | | | | | |
| | | Salt water | | | Plasmion | | | | | | |
| Sucrose % | AQUAKEEP % | 35° C. | | | 35° C. | | | B | | | C | | |
| | | G | Vo | To | G | Vo | To | G | Vo | To | G | Vo | To |
| --- | --- | --- | --- | --- | --- | --- | --- | --- | --- | --- | --- | --- | --- |
| 0 | 100 | 124 | 16 | 0,5 | 126 | 9,6 | 1 | 120 | 2,5 | 0 | 128 | 2,8 | 14 |

Table 1b shows the values of G, Vo and To for various mixtures of salt water, Plasmion and blood formula C recorded during the gelling test carried out at 35° C.

If a comparison is made of the sugar-superabsorbent synergies for absorption of the blood formulae, it is seen that wet mixing tends to increase the value of Vo. Synergy is noted for blood and to a lesser degree for salt water, when the maximum absorption capacity G is considered.

Plasmion gave values intermediate between salt water and blood.

EXAMPLE II

In order to verify the properties of the composition for different types of superabsorbent, mixtures were prepared of sugar and a superabsorbent, respectively a polyacrylate starch available under the brane name Sanwet, a synthetic polyacrylate prepared by an aqueous solution process and available under the brand name AQUALIC, a crosslinked carboxymethylcellulose available under the brand name AKUCELL, a synthetic polyacrylate prepared by an inverted suspension process and available under the brand name LUQUASORB, and a second synthetic acrylate prepared by an aqueous solution process and available under the brane name FAVOR.

The mixtures were dried, ground and screened as for example I.

(1) To facilitate the dispersion of the superabsorbent in the sugar syrup and improve the rheological qualities of the composition as it leaves the mixer, and its plastic properties after drying.

(2) To confer on the mixture specific qualities corresponding to its intended use, particularly in the treatment of wounds.

The incorporation of glycerol, isopropanol and polyethylene glycol, for example, correspond to the second aim.

Twenty-nine preparations were prepared by wet mixing sucrose and superabsorbent with various additives. The compositions are shown in table 3a. The proportions of additives mentioned correspond to the real values at the beginning of mixing.

These 29 preparations were subjected to the R30 retention test for salt water and for the blood formulae, and to the gelling (vortex) test for salt water, Plasmion and the blood formulaes. The results are shown in tables 3a and 3b.

Table 3b shows that it is possible to incorporate up to 6.5% of glycerol in the mixtures sucrose AQUAKEEP (see products 4 and 5 by comparison with product 3) and sucrose-Sanwet (see products 11 and 12 by comparison with product 10, and product 13 by comparison with product 14), while maintaining the degree of retention of blood of the compound without additive.

Table 3c shows an increase in theoretical gelling

TABLE 2a

| | | R30 retention test for blood formulae C and B | | | | | |
| Sucrose % | IRA % | SANWET | | AQUALIC | AKUCELL | LIQUASORB |
| | | C | B | C | C | C |
| --- | --- | --- | --- | --- | --- | --- |
| 93,5 | 6,5 | — | 13,5 | — | — | — |
| 90,9 | 9,1 | — | 15 | — | — | — |
| 80 | 20 | 12 | 9 | 11 | 11,5 | 16,5 |
| 70 | 30 | 11 | 11 | 8 | 11,5 | 13,5 |
| 0 | 100 | 6,5 | 6,5 | 4,5 | 13,5 | 8,5 |

TABLE 2b

| | | Vortex test | | | | | | Blood formulae 35° C. | | | | | |
| | | Salt water | | | Plasmion | | | | | | | | |
| Sucrose % | ANWET % | 35° C. | | | 35° C. | | | B | | | C | | |
| | | G | Vo | To | G | Vo | To | G | Vo | To | G | Vo | To |
| --- | --- | --- | --- | --- | --- | --- | --- | --- | --- | --- | --- | --- | --- |
| 93,5 | 6,5 | 60 | 1,4 | 0 | 60 | 1,7 | 1 | 130 | 2,3 | 0 | — | — | — |
| 90,4 | 9,1 | 94 | 3,6 | 0 | 82 | 6,2 | 9 | 164 | 5 | 8 | 180 | 4 | 0 |
| 85 | 15 | 132 | 2,9 | 0 | 115 | 3,4 | 2 | 126 | 3,9 | 6,5 | — | — | — |
| 80 | 20 | 108 | 3,5 | 0 | 76 | 3,8 | 4 | 123 | 2,7 | 0 | 150 | 2,2 | 0 |
| 70 | 30 | — | — | — | 94 | 3,4 | 8 | 100 | 3,0 | 11 | — | — | — |
| 0 | 100 | 114 | 3,5 | 0 | 86 | 2,1 | 0 | 72 | 0,5 | 0 | 80 | 0,4 | 0 |

It can be seen from these data tables that synergy for blood was again noted, whatever the superabsorbent used, both in terms of R30 values and G values.

EXAMPLE III

In this example, the properties of the mixtures were studied upon introduction of additives.

Additives may be admixed to some sucrose-superabsorbent compositions as a function of two distinct aims:

power G for blood and salt water, as in the preceding examples. Product 5 in particular, in the form of granules or flakes, meets the specifications of absorption capacity for use in the treatment of wounds in hospital or in the house.

Likewise, isopropanol can only be incorporated up to 8% (see 19 by comparison with 3, and 20 by comparison with 10), the glycerol-isopropanol mixture up to 9% (9 by comparison with 3, 16 by comparison with 10) and polyethylene glycol up to 8% (21 to 23 by comparison with 3, 22–24 by comparison with 10), without markedly affecting the performances of the corresponding sucrose-superabsorbent compositions.

The incorporation of additives with curative action, such as zinc oxides, debriding, antiseptic or biochemical acids (for example, lactic acid, sorbic acid, boric acid, etc.), vitamin and other cicatrizants, biological or plant extracts, amino acids, antiseptics of the povidone type or others, sulfamides, antibiotics, surfactants, etc., does not have any apparent effects on the performances of simple sugar-superabsorbent compositions when the usual recommended pharmacopeial quantities are used.

One particularly advantageous embodiment of the invention consists in adding to the mixture a protease specifically intended for treatment of wounds and blood. Composition 29 had this formula and showed reinforced activity by comparison with product 10. Note that during the manufacturing process, it was shown experimentally that the proteolytic capacity of the protease was preserved at 70% of the starting value.

TABLE 3a

| N° | Sucrose % | Composition AQUAKEEP (AK) SANWET (SW) % | Additives % | |
|---|---|---|---|---|
| 1 | 0 | AK | 100 | — |
| 2 | 0 | SW | 100 | — |
| 3 | 90,0 | AK | 9,1 | — |
| 4 | 87 | AK | 8,7 | GLYCEROL 4,3 |
| 5 | 85,1 | AK | 8,5 | " 6,4 |
| 6 | 73,6 | AK | 20 | " 6,4 |
| 7 | 80 | AK | 20 | — |
| 8 | 87 | AK | 8,7 | ISOPROPANOL 4,3 |
| 9 | 82,9 | AK | 8,3 | GLYCEROL 4,4 / ISOPROPANOL 4,4 |
| 10 | 90,9 | SW | 9,1 | — |
| 11 | 87 | SW | 8,7 | GLYCEROL 4,3 |
| 12 | 85,1 | SW | 8,5 | " 6,4 |
| 12 | 73,6 | SW | 20 | " 6,4 |
| 14 | 80 | SW | 20 | — |
| 15 | 87 | SW | 8,7 | ISOPROPANOL 4,3 |
| 16 | 82,9 | SW | 8,3 | GLYCEROL 4,4 / ISOPROPANOL 4,4 |
| 17 | 88,9 | AK | 8,9 | ISOPROPANOL 2,2 |
| 18 | 88,9 | SW | 8,9 | ISOPROPANOL 2,2 |

TABLE 3a-continued

| N° | Sucrose % | Composition AQUAKEEP (AK) SANWET (SW) % | Additives % | |
|---|---|---|---|---|
| 19 | 83,3 | AK | 8,3 | ISOPROPANOL 8,3 |
| 20 | 83,3 | SW | 8,3 | ISOPROPANOL 8,3 |
| 21 | 88,9 | AK | 8,9 | PEG 300 2,2 |
| 22 | 88,9 | SW | 8,9 | " 2,2 |
| 23 | 83,3 | AK | 8,3 | " 8,3 |
| 24 | 83,3 | SW | 8,3 | " 8,3 |
| 25 | 93,5 | AK | 6,5 | — |
| 26 | 93,5 | SW | 6,5 | — |
| 27 | 82,3 | AK | 5,4 | PEG 300 4,6 / ZnO 7,7 |
| 28 | 82,3 | SW | 5,4 | PEG 300 4,6 / ZnO 7,7 |
| 29 | 90,7 | SW | 9,1 | PROTEASE 0,18 |

TABLE 3b

R30 retention test

| | | Retention | | |
|---|---|---|---|---|
| | | | Bolld formulae 35° C. | |
| N° | Salt water 35° C. | A | B | C |
| 1 | 49 | 12 | 7 | 6 |
| 2 | 44 | — | 6,5 | — |
| 3 | 47 | 16,5 | 11 | — |
| 4 | — | — | — | — |
| 5 | — | — | — | — |
| 6 | — | — | 11 | — |
| 7 | 47 | — | 11 | — |
| 8 | — | — | — | — |
| 9 | — | 17,2 | — | — |
| 10 | — | — | 15 | — |
| 11 | — | 14 | — | — |
| 12 | — | 11 | — | — |
| 13 | — | — | 11 | — |
| 14 | 41,5 | — | 9 | 12 |
| 15 | — | 22,7 | — | — |
| 16 | — | 16 | — | — |
| 17 | — | 18,5 | — | — |
| 18 | — | 19 | 17,7 | — |
| 19 | — | — | — | — |
| 20 | — | — | — | — |
| 21 | — | — | — | — |
| 22 | — | — | — | — |
| 23 | — | — | — | — |
| 24 | — | — | — | — |
| 25 | — | 18 | 13,5 | — |
| 26 | — | — | 13,5 | — |
| 27 | — | — | — | — |
| 28 | — | — | — | — |
| 29 | — | 19 | — | — |

TABLE 3c

Gelling test, vortex
Vortex

| | Salt water 35° C. | Plasmion 35° C. | Bolld formulae 35° C. | | |
|---|---|---|---|---|---|
| | | | A | B | C |
| N° | G Vo To | G Vo To | G Vo To | G Vo To | G Vo To |
| 1 | 124 16 0,5 | 126 9,6 1 | — — — | 120 2,5 0 | 128 2,8 14 |
| 2 | 114 3,5 0 | 86 2,1 0 | — — — | 76 0,4 0 | — — — |
| 3 | 220 5,9 0 | 115 6,6 7 | — — — | 354 4 0 | 323 4,3 0 |
| 4 | 216 7 8 | 119 9,6 1,8 | 247 4,8 0 | — — — | — — — |
| 5 | 188 13,4 1 | 109 9,1 0 | — — — | — — — | — — — |
| 6 | 186 8,2 0 | 128 6,7 — | — — — | 237 2,4 0 | — — — |
| 7 | — — — | — — — | — — — | 149 2,9 0 | 315 2,7 0 |
| 8 | 206 10,9 8 | 250 2,7 0 | — — — | — — — | — — — |
| 9 | 147 24,1 14 | 212 2,8 0 | 423 2,2 0 | — — — | — — — |
| 10 | 94 3,6 0 | 82 6,2 9 | — — — | 164 5 8 | 180 4 0 |
| 11 | 132 4,3 0 | 104 9,4 13 | — — — | — — — | — — — |
| 12 | 154 6,2 0 | 121 5,2 2,1 | — — — | — — — | — — — |
| 13 | 136 3,4 0 | 91 3,3 2 | — — — | — — — | 69 122 50 |
| 14 | 108 3,5 0 | 76 3,8 4 | — — — | 123 2,7 0 | 150 2,2 0 |

TABLE 3c-continued

| | | | | | | | Gelling test, vortex Vortex | | | | | | | | |
|---|---|---|---|---|---|---|---|---|---|---|---|---|---|---|---|
| | | | | | | | | | Bolld formulae 35° C. | | | | | | |
| | Salt water 35° C. | | | Plasmion 35° C. | | | A | | | B | | | C | | |
| N° | G | Vo | To | G | Vo | To | G | Vo | To | G | Vo | To | G | Vo | To |
| 15 | 121 | 2,9 | 0 | 70 | 5,4 | 10 | 226 | 3,6 | 0 | — | — | — | — | — | — |
| 16 | 165 | 1 | 0 | 88 | 1,9 | 5 | 99 | 1,2 | 0 | — | — | — | — | — | — |
| 17 | 235 | 4,4 | 0 | 130 | 3,6 | 2,5 | 184 | 5,9 | 7 | — | — | — | — | — | — |
| 18 | 60 | 1,6 | 0 | 75 | 1,5 | 12 | 196 | 2,8 | 1,7 | — | — | — | — | — | — |
| 19 | 242 | 7,8 | 0 | 134 | 6,1 | 0 | — | — | — | — | — | — | — | — | — |
| 20 | 94 | 5,3 | 0 | 73 | 4,3 | 0 | — | — | — | — | — | — | — | — | — |
| 21 | 347 | 7,3 | 0 | 190 | 3,1 | 0 | — | — | — | — | — | — | — | — | — |
| 22 | 75 | 1,3 | 0 | 132 | 2,1 | 3 | — | — | — | — | — | — | — | — | — |
| 23 | 354 | 4,3 | 0 | 179 | 3,8 | 0 | — | — | — | — | — | — | — | — | — |
| 24 | 58 | 1,3 | 0 | 83 | 0,6 | 0 | — | — | — | — | — | — | — | — | — |
| 25 | 300 | 5,8 | 8 | 145 | 3,7 | 6 | — | — | — | 183 | 2,9 | 0 | 243 | 4,2 | 0 |
| 26 | 60 | 1,4 | 0 | 60 | 1,7 | 1 | — | — | — | 130 | 2,3 | 0 | — | — | — |
| 27 | 146 | 6,8 | 0,8 | 115 | 8,6 | 1,2 | — | — | — | — | — | — | — | — | — |
| 28 | 62 | 4,2 | 0 | 58 | 3 | 4,1 | — | — | — | — | — | — | — | — | — |
| 29 | 163 | 7,5 | 0 | 116 | 9,5 | 5 | — | — | — | — | — | — | — | — | — |

What is claimed is:

1. A process for the preparation of a composition which absorbs large quantities of liquids comprising the steps of
    (a) providing a concentrated solution of a saccharide in water;
    (b) adding a pre-determined quantity of a hydrophilic water-insoluble, water-swellable polymer to the solution of step (a);
    (c) kneading of the composition of step (b) to provide a homogeneous paste; and
    (d) drying the paste of step (c) to adjust the water content to a value ranging between about 2 and 15% water.

2. The process according to claim 1 wherein a plasticizer in a proportion of less than about 10% of the total mass prior to addition of the plasticizer is added to the composition of step (a) or step (b).

3. The process according to claim 2 wherein the plasticizer is selected from the group consisting of glycerol, polyethylene glycol, polyvinyl alcohol, isopropanol, and polyvinyl pyrrolidone.

4. The process according to any of claims 1 to 3 wherein a pharmaceutical additive is incorporated into the composition.

5. The process according to claim 4 wherein synthetic or natural fibers are incorporated into the composition during the kneading step.

6. The process according to claim 5 wherein sugar is incorporated dry into the composition in the form of powder.

7. The process according to claim 6 wherein the dry sugar is premixed with the polymer of step (b) before mixing of the polymer with the concentrated solution of step (a).

8. The process according to claim 7 wherein the dried paste produced in step (d) is applied to a support so as to form a composite structure.

9. The process according to claim 8 wherein the quantity of polymer of step (b) is selected so as to comprise less than about 50% of the total mass of the dried paste produced in step (d).

10. The process according to claim 9 wherein the saccharide is a mono-saccharide.

11. The process according to claim 9 wherein the saccharide is a di-saccharide.

* * * * *